United States Patent [19]

Abe et al.

[11] Patent Number: 4,469,879

[45] Date of Patent: Sep. 4, 1984

[54] TRICHLOROPOLYFLUORO-BICYCLO ETHERS

[75] Inventors: Takashi Abe, Kasugai; Hajime Baba, Nagoya; Eiji Hayashi, Kohnan; Shunji Nagase, Nagoya, all of Japan

[73] Assignees: Agency of Industrial Science and Technology; Ministry of International Trade & Industry, both of Tokyo, Japan

[21] Appl. No.: 458,038

[22] Filed: Jan. 14, 1983

[30] Foreign Application Priority Data

Feb. 12, 1982 [JP] Japan .................................. 57-21637

[51] Int. Cl.$^3$ ............................................ C07D 307/82
[52] U.S. Cl. ...................................... 549/465; 549/462
[58] Field of Search ............................... 549/462, 465

[56] References Cited

FOREIGN PATENT DOCUMENTS 1040846 8/1980 Japan .
1063316 11/1980 Japan .

OTHER PUBLICATIONS

Henne et al., Perfluorinated Cyclic Ethers, vol. 74, pp. 5420–5422, Nov. 1952.
Tiers, The Chemistry of Perfluoro Ethers. I. Substitution of α-Fluorine by Chlorine: The α,α,α'-Trichloro Perfluoro Ethers, vol. 77, pp. 4837–3840, Feb. 1955.

Primary Examiner—Henry R. Jiles
Assistant Examiner—Bernard Dentz
Attorney, Agent, or Firm—Oblon, Fisher, Spivak, McClelland & Maier

[57] ABSTRACT

Trichloropolyfluoro-bicyclo ethers are novel compounds, useful as a solvent or thermal medium for various pharmaceutical chemicals. They are produced by the reaction of perfluoro-bicyclo ether with anhydrous aluminum chloride.

10 Claims, No Drawings

TRICHLOROPOLYFLUORO-BICYCLO ETHERS

BACKGROUND OF THE INVENTION

1. Field of the Invention

This invention relates to novel compounds, trichloropolyfluoro-bicyclo ethres, suitable as solvents or thermal media and to a method for the manufacture of the compounds.

2. Description of the Prior Art

Polychloropolyfluoro-monocyclo ethers have been known to the art. As techniques for the manufacture of these compounds, there have been suggested (1) a method which resorts to chlorination of polyfluoro-monocycle ether (J. Am. Chem. Soc., Vol. 74, page 5420) and (2) a method which involves chlorination of perfluoro-monocyclo ether (J. Am. Chem. Soc., Vol. 77, page 4837), for example. To be specific, the method of (1) comprises photochemically chlorinating an α,α-,α',α'-tetrahydroperfluoro-monocyclo ether and the method of (2) comprises chlorinating a monocyclic perfluoro ether by the agency of anhydrous aluminum chloride.

Polychloropolyfluoro-bicyclo ethers which have a bicyclic configuration have not heretofore been known to the art.

The inventors of this invention conducted various studies on production of perfluoro compounds having a bicyclic configuration. They consequently succeeded in producing novel perfluoro-bicyclo ethers such as perfluoro-(7-oxa-bicyclo[4.3.0]nonane) and perfluoro-(2-oxa-bicyclo[3.3.0]octane) by electrolytically fluorinating a monocarboxylic acid having a cyclohexyl group or cyclopentyl group attached to an α-carbon atom thereof or a derivative of the carboxylic acid (Japanese Patent Publication No. SHO 55(1980)-045547 and No. SHO 55(1980)-032794). After further studies in the same field, they have now ascertained that the reaction of anhydrous aluminum chloride upon such a perfluoro-cyclo ether unexpectedly produces a novel partially chlorinated compound. The present invention has issued from this knowledge.

SUMMARY OF THE INVENTION

One object of the present invention is to provide trichloropolyfluoro-bicyclo ethers as novel useful compounds.

Another object of the present invention is to provide a method for the manufacture of trichloropolyfluoro-bicyclo ethers as novel useful compounds.

The present invention provides novel trichloropolyfluoro ethers represented by the general formula:

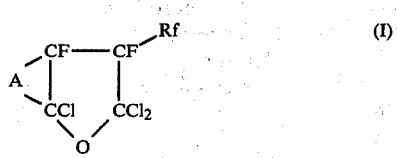

(wherein A denotes a hexafluoropropylene group or an octafluorobutylene group and Rf denotes a fluorine atom, a trifluoromethyl group, or a pentafluoroethyl group) and a method for the manufacture of trichloropolyfluoro ethers represented by the aforementioned general formula. The present method is characterized by mixing a perfluoro-bicyclo ether represented by the general formula:

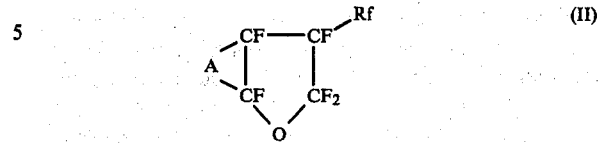

(wherein A and Rf have the same meanings as described above) with anhydrous aluminum chloride and heating the resultant mixture for inducing reaction.

DESCRIPTION OF PREFERRED EMBODIMENTS

The perfluoro-bicyclo ether represented by the general formula:

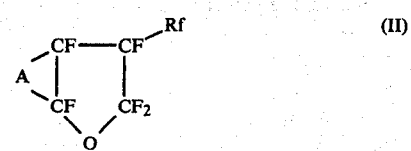

is a known compound which is used as the starting material for the manufacture of a trichloropolyfluoro-bicyclo ether represented by the general formula:

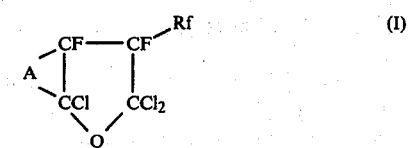

which is the novel compound of the present invention. This compound can be easily obtained by electrolytically fluorinating a monocarboxylic acid having a cyclohexyl group or a cyclopentyl group attached to an α-carbon atom thereof or acid chloride, methyl ester, or other similar derivative of the carboxylic acid.

The novel compound of this invention represented by Formula (I) is produced by mixing the perfluoro-bicyclo ether represented by Formula (II) with anhydrous aluminum chloride and heating the resultant mixture. Optionally, this reaction may be carried out in the presence of carbon tetrachloride as a medium.

Regarding the mixing ratio of the starting materials for the manufacture of the novel compound, namely of the perfluoro-bicyclo ether represented by Formula (II) and the anhydrous aluminum chloride, the aluminum chloride is used in an amount falling within the range of 1.5 to 3 moles per mole of the aforementioned ether.

When the amount of aluminum chloride falls short of reaching the lower limit 1.5 moles, the reaction velocity is lower than the tolerable level. When it exceeds the upper limit 3 moles, such undesirable by-products as carbon tetrachloride and hexachloroethane are formed to an excess.

The heating of the mixed reactants is carried out for the purpose of ensuring smooth progress of the reaction. For commercial operation of the manufacture, this heating is made at temperatures in the range of 150° to 180° C. When the heating temperature falls short of reaching the lower limit 150° C., the reaction velocity is lowered so much as to deprive the operation of its practicability. When the heating temperature exceeds the upper limit of 180° C., formation of such undesirable by-products as carbon tetrachloride, hexachloroethane, and hexachlorobenzene is accelerated and the yield of the product aimed at is lowered. When the reaction is carried out in the presence of carbon tetrachloride as a medium, it is required to be performed under application of pressure.

Even when the reaction is carried out in the presence of carbon tetrachloride, the proportion of the reactants participating in the reaction and the reaction temperature remain unchanged.

The aforementioned reaction of the present invention, though subject to the temperature condition and other factors, is normally performed for 16 to 24 hours to afford the trichlorinated compound aimed at by this invention in yields of 40 to 70%, for example.

The reaction described above produces a mixture containing therein the compound of the present invention. From this mixture, the compound of this invention can be separated by treating the mixture by any of the known methods such as, for example, fractionation or extraction. In the mixture from the reaction, there are contained hydrogen chloride, phosgene, carbon tetrachloride, hexachloroethane, hexachlorobenzene, aluminum chloride, aluminum fluoride, etc. besides the compound aimed at by this invention. The separation of this target compound can be easily accomplished by selecting a suitable measure of separation and purification in due consideration of the presence of these extraneous substances.

The novel compounds of the present invention are represented by the general formula (I). Specifically, they are perfluoro-(6,8,8-trichloro-7-oxa-bicyclo[4.3.0]nonane), perfluoro-(9-methyl-6,8,8-trichloro-7-oxa-bicyclo[4.3.0]nonane), perfluoro-(1,3,3-trichloro-2-oxa-bicyclo[3.3.0]octane), perfluoro-(4-methyl-1,3,3-trichloro-2-oxa-bicyclo[3.3.0]octane), and perfluoro-(4-ethyl-1,3,3-trichloro-2-oxa-bicyclo[3.3.0]octane), depending on the starting materials represented by the general formula (II).

In the formula (I) the chlorination occurs only at the specific position. This is because the reaction is participated in by the non-covalent electron pair of oxygen atom and, therefore, only the fluorine atom on the α carbon atom is substituted.

The trichloropolyfluoro-cyclo ether compounds to be obtained by the method of the present invention are substances never before reported in literature. They are colorless, transparent, odorless and thermally and chemically highly stable substances, which are highly useful as solvents and thermal media. Perfluoro-(6,8,8-trichloro-7-oxa-bicyclo[4.3.0]nonane), for example, readily produces perfluoro-(6-chloro-7-oxa-8-oxo-bicyclo[4.3.0]nonane) when it is caused to react with fuming sulfuric acid. These novel compounds are highly valuable intermediates for the production of useful derivatives. They are expected to find extensive utility in numeous other applications.

The novel compounds of this invention have been identified by measurement of boiling points, by gas chromatography, infrared absorption spectroscopy, $^{19}F$ nuclear magnetic resonance spectroscopy, and mass spectroscopy.

Now, the present invention will be more specifically described below with reference to working examples.

EXAMPLE 1

A stainless steel reaction tube having an inner volume of 30 ml and provided with a microvalve was charged with 2.8 g (7.4 m.mols) of perfluoro-(7-oxa-bicyclo[4.3.0]nonane) at a temperature of 165° C. for 20 hours for reaction.

The reaction product was first held standing at room temperature to expel therefrom gaseous by-products such as hydrogen chloride and phosgene. Then, the reaction product freed from the by-products was washed in small quantities several times with 1,2,2-trichloro-1,1,2-trifluoroethane to produce an extract. This extract was filtered to remove therefrom aluminum halogenide. The resultant filtrate was distilled under a vacuum to be freed from 1,2,2-trichloro-1,1,2-trifluoroethane. Consequently, there was obtained 2.1 g of perfluoro-(6,8,8-trichloro-7-oxa-bicyclo[4.3.0]nonane) (yield 71.7%).

The product of this invention obtained as described above on analysis by gas chromatography, infrared absorption spectroscopy, and $^{19}F$ nuclear magnetic resonance spectroscopy was identified to be the compound mentioned above. The boiling point of the substance was 174.8° to 175.0° C. and the refractive index, $n_D^{20}$, was 1.3833.

EXAMPLE 2

For 20 hours, 2.9 g (6.7 m.mols) of perfluoro-(9-methyl-7-oxa-bicyclo[4.3.0]nonane) and 1.8 g (13 m.mols) of anhydrous aluminum chloride were caused to react with each other at a temperature of 165° C. By following the procedure of Example 1, the reaction product was separated and purified and, on analysis, identified to be perfluoro-(9-methyl-6,8,8-trichloro-7-oxa-bicyclo[4.3.0]nonane) having a boiling point of 191.5° to 192.5° C. and a refractive index, $n_D^{20}$, of 1.3775). The yield was 49.0%.

EXAMPLE 3

For 20 hours, 1.8 g (5.4 m.mols) of perfluoro-(2-oxa-bicyclo[3.3.0]octane) and 1.5 g (11 m.mols) of anhydrous aluminum chloride were caused to react with each other at a temperature of 165° C. By following the procedure of Example 1, the reaction product was separated and, on analysis, identified to be perfluoro-(1,3,3-trichloro-2-oxa-bicyclo[3.3.0]octane) having a boiling point of 153.0° to 153.5° C. and a refractive index, $n_D^{20}$, of 1.3831. The yield was 63.3%.

EXAMPLE 4

For 22 hours, 1.7 g (4.0 m.mols) of perfluoro-(4-ethyl-2-oxa-bicyclo[3.3.0]octane) and 1.1 g (8 m.mols) of anhydrous aluminum chloride were caused to react with each other at a temperature of 165° C. By following the procedure of Example 1, the reaction product was separated and, on analysis, identified to be perfluoro-(4-ethyl-1,3,3-trichloro-2-oxa-bicycle[3.3.0]octane) having a boiling point of 188.5° to 189.0° C. and a refractive index, $n_D^{20}$, of 1.3750). The yield was 55.4%.

EXAMPLE 5

For 20 hours, 1.8 g (4.8 m.mols) of perfluoro-(7-oxa-bicyclo[3.3.0]nonane) and 1.3 g (10 m.mols) of anhydrous aluminum chloride were caused to react with each other in the presence of 3 ml of carbon tetrachloride at a temperature of 165° C.

By following the procedure of Example 1, the reaction product was separated and purified and, on analysis, identified to be perfluoro-(6,8,8-trichloro-7-oxa-bicyclo[4.3.0]nonane). The yield was 69.6%.

EXAMPLE 6

For 20 hours, 1.5 g (4.0 m.mols) of perfluoro-(7-oxa-bicyclo[4.3.0]nonane) and 1.0 g (7.5 m.mols) of anhydrous aluminum chloride were caused to react with each other at a temperature of 180° C.

By following the procedure of Example 1, the reaction product was separated and purified and, on analysis, identified to be perfluoro-(6,8,8-trichloro-7-oxa-bicyclo[4.3.0]nonane). The yield was 45.7%.

What is claimed is:

1. A trichloropolyfluoro-bicyclo ether of the formula:

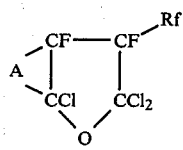

wherein A is one member selected from the class consisting of a hexafluoropropylene group and an octafluorobutylene group and Rf is one member selected from the class consisting of a fluorine atom, a trifluoromethyl group, and a pentafluoroethyl group.

2. The trichloropolyfluoro-bicyclo ether of claim 1 wherein A is a hexafluoropropylene group and Rf is a fluorine atom.

3. The trichloropolyfluoro-bicyclo ether of claim 1 wherein A is an octafluorobutylene group and Rf is a trifluoromethyl group.

4. The trichloropolyfluoro-bicyclo ether of claim 1 wherein A is a hexafluoropropylene group and Rf is a pentafluoroethyl group.

5. The trichloropolyfluoro-bicyclo ether of claim 1 wherein A is a octafluorobutylene group and Rf is a pentafluoroethyl group.

6. The trichloropolyfluoro-bicyclo ether of claim 1 which is perfluoro-(6,8,8-trichloro-7-oxa-bicyclo-(4,3,0)-nonane).

7. The trichloropolyfluoro-bicyclo ether of claim 1 which is perfluoro-(9-methyl-6,8,8-trichloro-7-oxa-bicyclo-(4,3,0)-nonane.

8. The trichloropolyfluoro-bicyclo ether of claim 1 which is perfluoro-(1,3,3-trichloro-2-oxa-bicyclo-(3,3,0)-octane.

9. The trichloropolyfluoro-bicyclo ether of claim 1 which is perfluoro-(4-methyl-1,3,3-trichloro-2-oxa-bicyclo-(3,3,0)-octane.

10. The trichloropolyfluoro-bicyclo ether of claim 1 which is perfluoro-(4-ethyl-1,3,3-trichloro-2-oxa-bicyclo-(3,3,0)-octane.

* * * * *